(12) United States Patent
Ziegler et al.

(10) Patent No.: US 6,179,767 B1
(45) Date of Patent: Jan. 30, 2001

(54) FOCUSSING OF THERAPEUTIC RADIATION ON INTERNAL STRUCTURES OF LIVING BODIES

(75) Inventors: James Francis Ziegler, Yorktown Heights; Robert Jacob von Gutfeld, New York, both of NY (US)

(73) Assignee: International Business Machines Corporation, Armonk, NY (US)

(*) Notice: Under 35 U.S.C. 154(b), the term of this patent shall be extended for 0 days.

(21) Appl. No.: 09/241,503

(22) Filed: Feb. 1, 1999

(51) Int. Cl.[7] .................................................. A61B 5/00
(52) U.S. Cl. ..................................... 600/1; 600/439
(58) Field of Search ........................... 600/1, 424, 439, 600/461, 462

(56) References Cited

U.S. PATENT DOCUMENTS

| | | | |
|---|---|---|---|
| 4,986,259 | * | 1/1991 | Aida et al. ............................ 600/439 |
| 5,452,720 | * | 9/1995 | Smith et al. ............................ 600/1 |
| 5,755,746 | * | 5/1998 | Lifshey et al. ......................... 607/50 |
| 5,984,853 | * | 11/1999 | Smith ...................................... 600/1 |

* cited by examiner

Primary Examiner—Max Hindenburg
(74) Attorney, Agent, or Firm—Casey P. August

(57) ABSTRACT

This invention helps achieve accurate focussing of therapeutic radiation at an internal structure (e.g. cancerous organ), which is often substantially movable within a living body. For this purpose, suitable sensors are laproscopically or surgically implanted at the location of the organ. These sensors may include semiconductor materials, scintillation materials, piezo-acoustic materials, x-ray emitters, or other materials which emit a signal when they are scanned by a beam of harmless investigative radiation, such as low intensity therapeutic radiation. The emitted signal is then monitored via implanted wires or light fibers or via external detectors during scanning to determine the targetted location at which a signal maximum occurs, whereupon the desired intensity of therapeutic radiation is focussed on this targetted location.

15 Claims, 2 Drawing Sheets

FOCUSSING OF THERAPEUTIC RADIATION ON INTERNAL STRUCTURES OF LIVING BODIES

CROSS-REFERENCE TO RELATED APPLICATIONS

This application is related to application Ser. No. 09/241,506 entitled "IMAGING OF INTERNAL STRUCTURES OF LIVING BODIES BY SENSING IMPLANTED MAGNETIC DEVICES", filed on the same date herewith, by Robert J. von Gutfeld and James F. Ziegler, which application is incorporated herein by reference.

FIELD OF THE INVENTION

The present invention relates to the treatment of organs, tumors, and other internal structures of living bodies with therapeutic radiation.

The present invention relates preferably to the field of radiation oncology, but it can also have other applications. The purpose of the invention is to be able to locate accurately the region or regions requiring radiation therapy within a patient even when the patient has undertaken any kind of motion or movement. As will be appreciated, it is very important to localize a therapeutic radiation treatment beam, i.e. align the beam accurately with the volume to be irradiated. Otherwise, adjacent healthy portions of the body may be injured by therapeutic radiation which is intended for the target organ, tumor, or other internal structure of a living body, In radiation therapy for the treatment of tumors or cancers, there is the problem of knowing the exact position (localization) of an internal organ or other internal structure to be irradiated because of natural movement of that internal structure within the body cavity. For example, the prostate or ovaries that are to undergo irradiation may move within the body cavity up to a centimeter between treatments.

Typically, preparation for radiation treatment includes obtaining tomographic images of the tumor a and surrounding tissue, usually recorded several days prior to the onset of radiation treatment. The 3-D reconstructieon of the images results in accurately locating the tumor in relation to the body as a whole. However, since radiation treatment may occur over a matter of months, there can be considerable shifts or displacements of the organ-containing tumor from the position originally determined from the tomograph. As a result, relying on the original tomographic positioning data can result in the radiation beam missing the target (tumor or other internal structure) either partially or even completely, and instead striking healthy tissue portions of the body that are not meant to be irradiated.

The present invention discloses the use of various types of implantable sensors and methods of locating internal body structures by communicating externally the instantaneous radiation at their locations.

BACKGROUND OF THE INVENTION

In general, the locations of internal tumors are obtained using CAT or MRI scans. However, these tumors within the body cavity may move due to motion of the patient (gravity pressure) or due to gastrointestinal pressures. It is essential to limit the treatment irradiation to the tumor site, and prevent irradiation of nearby healthy tissue. This is especially true for some organs, e.g. a liver, which may lie next to organs such as ovaries which are highly sensitive to radiation A method of locating an internal injury is disclosed in U.S. Pat. No. 5,755,746 issued on May 26, 1998 to Arthur Lifshey et al. This approach involves positioning, at an external location that is approximately adjacent to the internal injury, a marker that is visualizable by X-rays, magnetic resonance, or ultrasonic waves. This approach appears to lack accuracy for tumors and other internal structures because the marker is external (and thus distant) from the internal injury, and because internal structures are likely to move within the body.

SUMMARY OF THE INVENTION

The present invention broadly provides a method of therapeutic treatment of an internal structure of a living body with therapeutic radiation which comprises the steps of:

a) implanting, at the aforesaid internal structure, a sensor to identify a selected location of the internal structure, the sensor being capable of emitting a signal in response to irradiation thereof by a beam of an investigative radiation, b) scanning a region of the living body which includes the aforesaid internal structure with a beam of the aforesaid investigative radiation of a sufficiently low intensity to avoid causing injury to portions of the aforesaid region that are adjacent to the internal structure, c) measuring the aforesaid signal to determine occurrence of a maximum intensity of that signal during scanning stop (b), d) associating the aforesaid maximum intensity with a corresponding scanned location of the aforesaid region, and e) focussing a selected intensity of the therapeutic radiation at a target determined from the aforesaid corresponding scanned location of the aforesaid region.

According to a preferred embodiment of the invention, the aforesaid investigative radiation may comprise the aforesaid therapeutic radiation itself.

The present invention also provides a system for therapeutic treatment of an internal structure of a living body with therapeutic radiation after implantation, at the aforesaid internal structure, of a sensor to identify a selected location of the internal structure, the sensor being capable of emitting a signal in response to irradiation thereof by a beam of investigative radiation. This inventive system comprises:

a) a beam projector for scanning a region of the living body which includes the aforesaid internal structure with a beam of the aforesaid investigative radiation of a sufficiently low intensity to avoid causing injury to portions of the region that are adjacent to the internal structure, b) a signal measurement device for measuring said signal to determine occurrence of a maximum intensity of the aforesaid signal during scanning of the aforesaid region by the beam projector, c) a computing apparatus for associating the aforesaid maximum intensity with a corresponding scanned location of the region, and d) a controlled source of therapeutic radiation for focussing a selected intensity of the therapeutic radiation at a target determined from the aforesaid corresponding scanned location of the aforesaid region.

Where the aforesaid investigative radiation comprises the therapeutic radiation itself, then the afore controlled source of therapeutic radiation can serve as the aforesaid beam projector by projecting only a low intensity beam during investigative scanning of the aforesaid body region to identify the location of the implanted organ, tumor or other internal structure.

According to one preferred embodiment of the invention, the aforesaid sensor comprises a semiconductor diode capable of producing electric signals of an intensity that varies with the intensity of investigative radiation impinging upon said sensor during scanning of said region by said beam. For this purpose, the sensor includes wires implanted in the living body and extending to the surface of the body (e.g. to a connector at the navel) for connecting the semiconductor diode to an ammeter or other electric signal measurement device.

According to another embodiment, the sensor comprises a scintillator material capable of producing light signals of an intensity that varies with the intensity of investigative radiation impinging upon said sensor during scanning of said region by said beam. This type of sensor comprises light- transmitting fibers connecting the scintillator material to a suitable light signal measurement device.

According to an alternative embodiment of the invention, the sensor comprises a piezoelectric material capable of producing acoustic signals of an intensity that varies with the intensity of investigative radiation impinging upon the sensor during scanning of the body region by the investigative beam. In this case, the signal measurement device comprises an acoustic microphone which is disposed external to said living body to detect a maximum of the acoustic signals during beam scanning.

Alternatively, the sensor comprises a piezoelectric material capable of producing electrical signals of an intensity that varies with the intensity of investigative radiation impinging upon said sensor during scanning of said region by said beam. In this case, the sensor comprises wires implanted in the living body for connecting the piezoelectric material to an electric signal measurement device (e.g. via a surface connector at the navel).

As a further alternative embodiment, the sensor comprises an x-ray emitting material capable of producing x-ray signals of an intensity that varies with the intensity of investigative (e.g. therapeutic) radiation impinging upon sensor during scanning of said region by said beam; in this case, the signal measurement device comprises an x-ray detector which is located external to the living body.

BRIEF DESCRIPTION OF PREFERRED EMBODIMENTS

Figure 1:
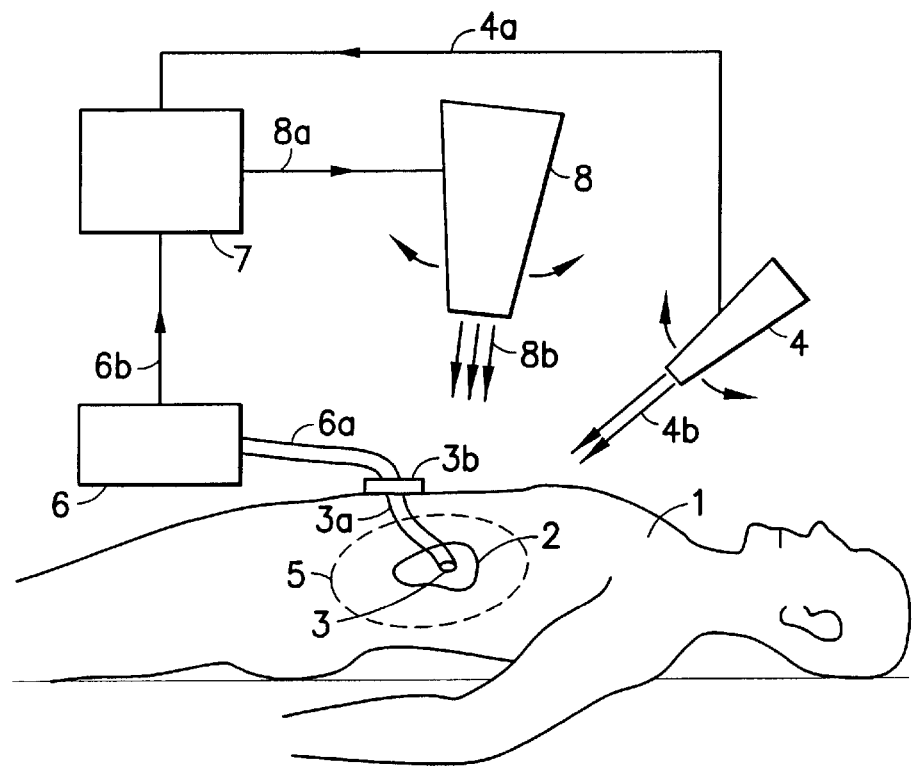
FIG. 1 is a schematic view of a system for therapeutic treatment of an internal structure of a living body with therapeutic radiation, according to a preferred embodiment of the present invention.

FIG. 1 shows a therapeutic radiation treatment system in which a human patient's living body 1 contains an internal structure 2, such as a cancerous prostate, which has significant freedom to move within the body from one treatment session to the next. This freedom of movement makes it difficult to consistently target the prostate while avoiding injury to adjacent healthy tissue portions of the body.

According to the invention, a sensor 3 (together with its connecting wires 3a and socket connector 3b) is implanted surgically or laproscopically at the center or other selected location of internal structure 2. The function of sensor 3 is to emit a signal when it is subsequently irradiated during scanning of region 5 (which includes internal structure 2) with a beam 4b of investigative radiation from beam projector 4. The beam 4b of investigative radiation is of sufficiently low intensity, below normal organic damage thresholds, to preclude injury to to portions of region 5 which are adjacent to the prostate or other internal structure 2.

Figure 2:
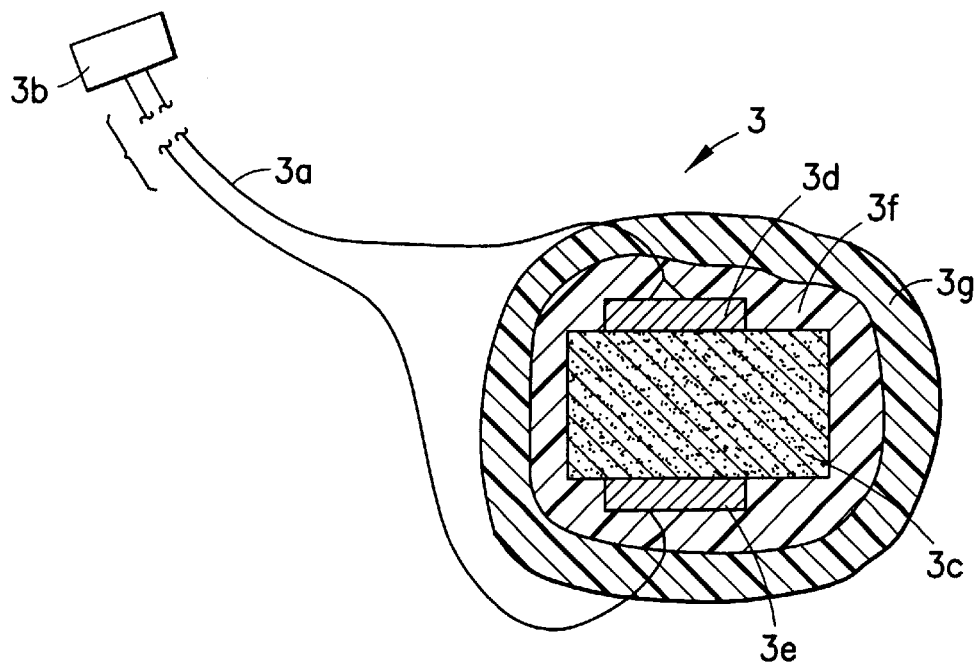
FIG. 2 is a schematic cross-sectional view of one type of sensor which may be used with the novel system depicted in FIG. 1.

The signal from sensor 3 is carried to a signal measurement device 6 which, at each therapeutic treatment session, is connected to wires 3a by connecting wires 6a to connector 3b, which may conveniently be located in the navel of the patient's body. Measurement device 6 detects the maximum intensity of the signal emitted by sensor 3 during scanning of region 5 and simultaneously transmits an electric signal defining that maximum intensity via connecting wires 6b to a computing apparatus, such as controller 7. Via wires 4a, controller 7 also simultaneously receives electric signals defining the instantaneous target being scanned by investigative beam 4b. Based on the simultaneous signals received, defining the instantaneous target of beam 4b (via wires 4a) and the corresponding instantaneous response signal from sensor 3 (via wires 6b), controller 7 controls the intensity and direction of therapeutic radiation 8b emitted by controlled source 8 via connecting wires 8a. When the signal from sensor 3 reaches a maximum intensity, source 8 is thus caused by controller 7 to project a full selected intensity of therapeutic radiation at the instantanteous target of beam projector 4, which is arranged to always correspond to the instantaneous target of source 8. FIG. 2 shows a semiconductor embodiment of a sensor 3 in the form of a semiconductor diode, including a doped silicon substrate 3c, an aluminum surface contact layer 3d, and a gold surface contact layer 3e. As shown in FIG. 2, sensor 3 comprises an insulating coating 3f of electrically insulating material and an outside coating 3g of a biologically inert material, such as polyethylene or PMMA (polymethyl methacrylate). Sensor 3 includes connecting wires 3a that connect contact layers 3d and 3e to connector 3b, which may be located in a patient's navel or elsewhere on the surface of the body. Although not illustrated in the schematic drawings herein, it will be understood that the wires 3a may be suitably sheathed with any required layers, such as an electrically insulating material to prevent leakage losses of the signal from sensor 3, a rigid conduit sheathing structure for any required structural strength, and a biologically inert outer coating (e.g. PMMA) to prevent chemical interaction with the patient's body.

As will be understood, sensors may take on many alternative forms, such as semiconductors, scintillators, x-ray emitters, piezoacoustic materials, piezoelectric materials, photovoltaics, and capsules of radiation chemicals which may be implanted at the center or other selected location of an organ, tumor or other internal structure requiring radiation therapy. These sensors respond to low levels of irradiation with a maximum intensity signal indicating that the irradiation beam is on-target. These sensors allow the precise alignment of the irradiation beam with the target tumor or organ (called "beam localization"). For all these cases, the sensor is implanted laproscopically or surgically prior to the radiation treatment. For electrical signals, a wire is used to communicate the sensor signals through the skin to a signal measurement device. For light emitting sensors, a light pipe runs between the sensor and external to the body by exiting through the skin of the patient. For capsules of radiation-sensitive chemicals, usually optical attenuation may be used to identify the sensor changes. This change may be achieved by paired light fibers, one bringing in a light source, and the other returning the attenuated light. For x-ray sensors, there is no need for a signal wire as the x-rays will exit the body and can be directly sensed externally. For piezo implants, the low level beam can be pulsed so that when it strikes the piezo, electrical signals are generated giving rise to an output from the piezo via the wires leading to an externally located sensor when the output is electrical.

For acoustic output, no wires are required. Rather, the signal measurement device may include a sensitive microphone, tuned to the resonant frequency of the piezo crystal. Movement of the microphone external to, but preferably on the surface of, the body causes the amplitude of the received acoustic wave to vary. When there is no bony structure between the piezo and the microphone, the maximum signal will generally be the one that is closest to the piezo and hence defines the ray along which the radiation beam should be aimed.

After radiation therapy is completed, the sensor may be removed from the subject or be allowed to remain as a passive inert body.

Figure 3:
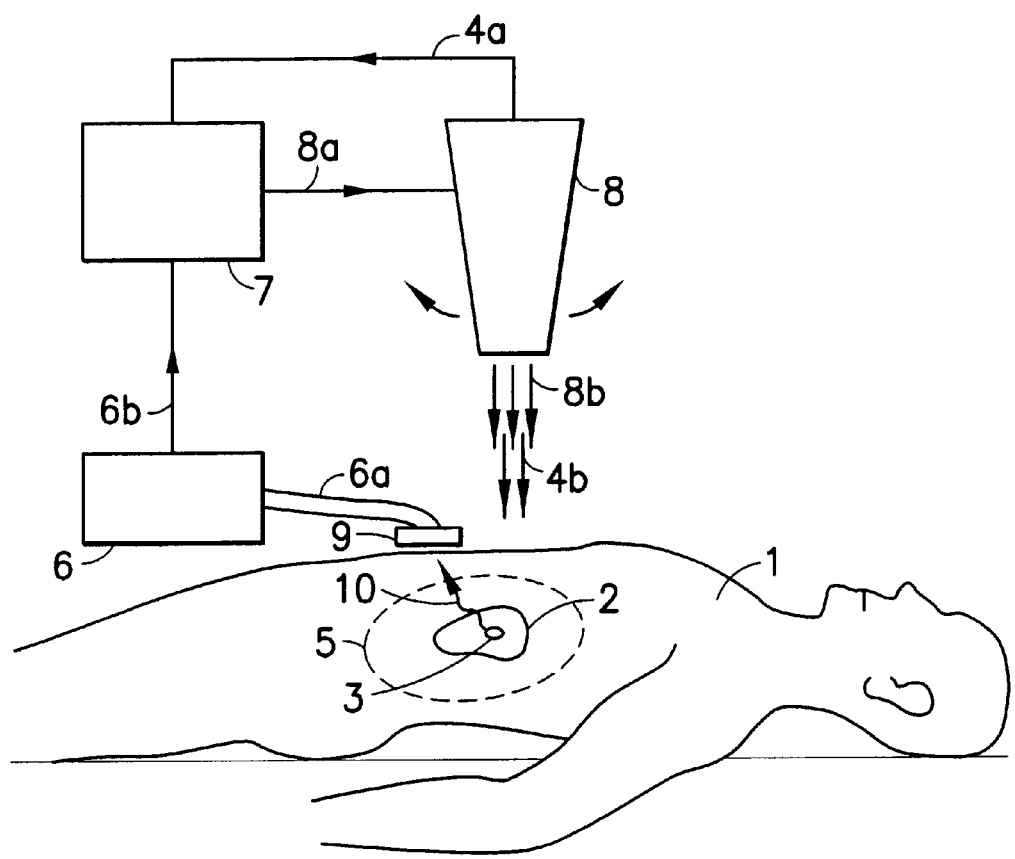
FIG. 3 is schematic view of a system for therapeutic treatment of an internal structure of a living body with therapeutic radiation, according to another preferred embodiment of the present invention, wherein therapeutic radiation, at low intensity, also serves as investigative radiation.

FIG. 3 shows another embodiment of a therapeutic treatment system in accordance with the present invention. The system shown in FIG. 3 differs from the system shown in FIG. 1 in two respects.

Firstly, sensor 3 of FIG. 3 is of a type that requires no wires to carry its signals to a suitable measurement device 6 at the exterior of body 1. For example, sensor 3 may comprise a piezoacoustic material which emits an acoustic signal 10 which is detected by a microphone 9.

Alternatively, sensor 3 of FIG. 3 may comprise a small amount of an X-ray emitter material (e.g. Ta, Pt, Au) in a biologically inert enclosure. Upon irradiation by a scanned beam of investigative radiation, sensor 3 will emit X-rays 10 which can be detected by a suitable X-ray detector 9 of measurement device 6.

Secondly, the embodiment of FIG. 3 employs therapeutic radiation as both investigative radiation (at a suitably low intensity level) and as therapeutic radiation (at a suitably high intensity level). For this purpose, FIG. 3 shows that source 8 first scans region 5 of body 1 with a beam 4b of a non-injuriously low intensity of therapeutic radiation, while simultaneously transmitting electrical signals via wires 4a to define locations of region 5 that are being scanned. These signals from wires 4a and electrical signals from wires 6b are associated by a computing apparatus shown as controller 7 to relate locations of region 5, which are then being scanned by low intensity therapeutic radiation 8b from source 8, with corresponding signals being simultaneously emitted by sensor 3. When the signal via wires 6b reaches a maximum intensity, controller 7 causes source 8 to focus a selected high intensity of therapeutic radiation at a target image determined from the corresponding location of region 5 which generated the maximum intensity signal.

As will be understood, if sensor 3 is implanted at an apex of a triangular prostate of known size, the maximum signal will define the location of the sensor 3 at that apex and will help controller 7 to focus therapeutic radiation from source 8 at an appropriate triangular image extending from sensor 3 at one apex.

Of course, it may be preferred to use other sensor arrangements which involve a plurality of sensors distributed in a selected pattern around or within the tumor or other internal structure.

While many different types of sensors 3 and corresponding signal measurement devices 6 may be used, a few exemplary choices will now be discussed briefly.

Example I

Semiconductor Detector as a Sensor

A small semiconductor sensor, processed to have diode characteristics, is implanted at the irradiation site. The sensor is encapsulated in a biologically passive container and is attached to two small diameter wires which provide bias and signal sensing. When the incident beam strikes the semiconductor it creates electron/holes as the beam particles transit the sensor. A single particle usually will create a sufficiently large pulse of electrons for external sensing so that ultra-low beam intensities may be used for the localization of the beam to the tumor volume. This allows full alignment of the beam to the tumor volume without any biological damage. For abdominal tumors, the wires might be led to the navel area of the body for termination. A suitable connector may be installed in this cavity for the duration of the treatment. After treatment, the connector may be removed, leaving the sensor and wires permanently inside, or the sensor and wires may be removed by standard or laproscopic surgery techniques.

More particularly, the sensor may comprise a semiconductor material, such as silicon, intrinsically doped to high resistivity. For silicon, this can be crystalline silicon lightly doped with boron to a resistivity over 1000 ohm-cm. Construction is in the form of a small planar shape, 1 mm×1 mm, about 0.2 mm thick. One surface contact is, for example, an aluminum layer deposited on the silicon. The contact on the opposite surface is, for example a gold layer. This structure will have silicon diode characteristics, well known in the semiconductor art. The diode is coated with an insulating material, and then with a bio-inert material to allow its safe insertion into body cavities. The sensor is connected by two wires to either an implanted telemetry device, or by thin wires extending outside the body. By applying a voltage bias between the two metal layers, negative bias to the gold layer, of the order of 25V, a significant depletion region will be induced in the semiconductor. This depletion region will be very sensitive to any radiation, creating (for silicon) one electron-hole pair for every 3.6 eV of energy absorbed by the silicon from the radiation. Hence a single charged particle (e.g. photon (such as gamma or x-ray) or proton) of 100 keV, may create about 5 femto coulumbs of charge, which will be swept out by the diode bias into a single pulse less than 100 ns wide. By differentiating the output from the diode, the natural ambient noise will be significantly reduced and this singular pulse may be amplified and detected. Since individual particles may be detected, extremely small radiation levels may be identified and localized. Since a treatment dose may be of the order of 1000 RADs, i.e. perhaps 2×E10 protons at 200 Mev, the detection dose may be 1/1E6 of this dose allowing very accurate detection statistics without imparting any significant radiation dose to the patient during the sensor locating cycle.

Since a total radiation dose rarely exceeds 10,000 RADs, the sensor will survive repeated exposures ("fractions"). Such semiconductor sensors have been shown to detect a single beam particle and yet are robust enough to survive even the most intense radiation treatments (10,000 rads), see IEEE Trans. Nucl. Sci., 45, 508–511 (1998). For example, silicon diodes are well known to remain robust to proton doses exceeding 5E12 protons/cm2. However, 10,000 RADs are reached with only 2E11 protons/cm2 at 200MeV, leaving a wide margin between sensor degradation and any normal treatment schedule Example II A Piezoelectric Material as a Sensor A small piece of piezo material (typically a few mm on the side, and preferably a thickness equal to a ½ wavelength of its resonant acoustic frequency ) may be used as a sensor. This sensor would not need to be directly connected to an external connector. The sensor is encapsulated in a biologically passive container. When the incident beam strikes the piezo material it emits acoustic waves as the beam particles transit the sensor (common crystals such as silicon may be used, although ferro-magnetic and ferro-electric materials may have higher efficiencies). This sensor is less sensitive than the semiconducor sensor of Example I, but is capable of sensing beam currents of about 0.1 pico-Amp (<6,000,000 charged particles/sec), several orders of magnitude below biological damage levels. Thus, ultra-low beam intensities may be used for the localization of the beam to the tumor volume. This allows full alignment of the beam to the tumor volume without any biological damage. For a variety of tumors such as abdominal ones, the acoustic signals may be picked up by a microphone acoustically coupled to the skin. Since the acoustic radiation is in the ultra-high frequency band, it should not be affected by normal biological noises. After treatment, the sensor may be left permanently inside the patient. In general, the microphone is moved until a maximum signal strength is sensed. This will generally define the position very close to the position along which the radiation treatment beam should be directed.

Example III

Scintillation Materials as a Sensor

A small scintillator sensor connected to a light fiber can be implanted at the irradiation treatment site. The sensor is encapsulated in a biologically passive container. When the incident beam strikes the scintillator it creates light pulses as the beam particles transit the sensor. While this sensor is less sensitive than the semiconductor sensor, of Example I above, it is capable of sensing beam currents of <1 femto-Amp (<6000 charged particles/sec), which are many orders of magnitude below biological damage levels. Thus, ultra-low beam intensities may be used for the localization of the beam to the tumor volume. This allows full alignment of the beam to the tumor volume without any biological damage. For abdominal tumors, the light fiber might be led to the bellybutton area for termination. A suitable connector may be installed in this cavity for the duration of the treatment. After treatment, the connector may be removed, leaving the sensor and wires permanently inside, or the sensor and wires may be removed by laproscopic surgery.

For example, the sensor can be made with a small scintillator offered by Bicron Inc. of Newbury, Ohio, United States of America as their product BC-400 or BC-404, which takes the form of a plastic scintillator material, 1mm thick. This sensor is coated with an opaque layer, followed by a bio-inert layer. The sensor is connected to a non-scintillating (or very reduced scintillating) optical fiber such as the Bicron Inc. fiber wave guide BCF-98. These fibers have a polystyrene core coated with a PMMA layer for bio-neutrality. Under a weak investigative radiation beam the scintillator produces light which is carried by the optical fiber externally to a measurement device 6 (see FIG. 1) comprising a suitable frequency filter followed by an optical sensor, such as a electron multiplier tube, in a manner well known to those skilled in the art. The electrical signal from the electron multiplier tube is then sent to computing apparatus 7 via wires 6b to help direct the therapeutic radiation from source 8.

Example IV

X-ray Emitting Material as a Sensor

A small x-ray emitter material may be used as a sensor and need not be directly connected to an external connector. The sensor is encapsulated in a biologically passive container. When the incident beam strikes the material it emits x-rays as the beam particles transit the sensor (the x-ray emitter may be made of any heavy material, e.g. Ta, Pt or Au, which emits x-rays which exit the body without significant absorption). While this sensor may be less sensitive than the semiconductor sensor of Example I , it is capable of sensing beam currents of about 0.1 nano-Amp (<6×10E9 charged particles/sec), which is well below biological damage levels. Thus reduced beam intensity may be used for the localization and correct focussing of the therapeutic beam to the tumor volume or the internal structure. This allows full alignment of the beam to the tumor volume without any biological damage. For abdominal tumors, the x-rays may be picked up by a standard x-ray detector placed near the body and connected to the controller of the source of therapeutic radiation. After treatment, the sensor may be left permanently inside the patient.

Example V

Radiation-Sensitive Precursor Material as a Sensor

A small capsule of radiation-sensitive precursors may be used as a sensor encased in a module which allows the detection of the radiation-induced chemical changes. For example, the sensor may be made of a super-saturated polymer precursor, which undergoes compound formation under radiation and expands. Such a material would be encased in the module with a pressure sensitive transducer. Other possible precursors might produce heat, light or changes in optical characteristics. These would be encased with their respective requisite transducer. When the incident beam strikes the capsule, its transducer responds with an electrical signal proportional to the amount of radiation conversion. This electrical signal is then transmitted to the controller for focussing therapeutic radiation, as described for the semiconductor sensor of Example I.

As will be understood, the present invention discloses the use of embedded sensors that respond to the incident radiation and emit a signal that can be detected externally. This signal assures that the therapeutic radiation is correctly localized to a target determined from the scanned location of the sensor. This localization may be done by scanning a sensor-containing region of the body with a very dilute investigative beam, below organic damage thresholds, and identifying the parameters of the location being scanned at the moment that a maximum signal is emitted in order to direct the intense therapeutic treatment beam directly to the tumor site.

This invention utilizes various sensors which may be implanted within an animate body. The sensors respond to incident low-level radiation. Further, mechanisms are disclosed to communicate the response signals of the sensor outside the body so that they may be used for irradiation diagnostics.

While the present invention has been described with reference to preferred embodiments in order to facilitate a better understanding of the invention, those skilled in the art will recognize that the invention can be embodied in various ways without departing from the scope and spirit of the invention as set forth in the appended claims.

What is claimed is:

1. A method of therapeutic treatment of an internal structure of a living body with therapeutic radiation, said method comprising the steps of:
    a) implanting, at said internal structure, a sensor to identify a selected location of said internal structure, said sensor being capable of emitting a signal in response to irradiation thereof by a beam of an investigative radiation,
    b) scanning a region of said living body which includes said internal structure with a beam of said investigative radiation of a sufficiently low intensity to avoid causing injury to portions of said region that are adjacent to said internal structure,
    c) measuring said signal to determine occurrence of a maximum intensity of said signal during scanning step (b),
    d) associating said maximum intensity with a corresponding scanned location of said region, and
    e) focussing a selected intensity of said therapeutic radiation at a target determined from said corresponding scanned location of said region.

2. A method as set forth in claim 1, wherein said investigative radiation comprises said therapeutic radiation.

3. A method as set forth in claim 2, wherein said sensor comprises a semiconductor diode capable of producing electric signals of an intensity that varies with the intensity of investigative radiation impinging upon said sensor during scanning of said region by said beam.

4. A method as set forth in claim 3, wherein said measuring step c) is carried out with wires implanted in said living body, said wires connecting said semiconductor diode to a location which is external to said living body.

5. A method as set forth in claim 2, wherein said sensor comprises a scintillator material capable of producing light signals of an intensity that varies with the intensity of investigative radiation impinging upon said sensor during scanning of said region by said beam, and wherein said measuring step c) is carried out with light-transmitting fibers connecting said sensor to a location which is external to said living body.

6. A method as set forth in claim 2, wherein said sensor comprises a piezoelectric material capable of producing acoustic signals of an intensity that varies with the intensity of investigative radiation impinging upon said sensor during scanning of said region by said beam, and wherein said measuring step c) is carried out with an acoustic microphone which is disposed external to said living body.

7. A method as set forth in claim 2, wherein said sensor comprises an x-ray emitting material capable of producing acoustic signals of an intensity that varies with the intensity of investigative radiation impinging upon said sensor during scanning of said region by said beam, and wherein said measuring step c) is carried out with an x-ray detector which is disposed external to said living body.

8. A system for therapeutic treatment of an internal structure of a living body with therapeutic radiation, said system comprising:
    a) a sensor implanted to identify a selected location of said internal structure, said sensor being capable of emitting a signal in response to irradiation thereof by a beam of investigative radiation,
    b) a beam projector for scanning a region of said living body which includes said internal structure with a beam of said investigative radiation of a sufficiently low intensity to avoid causing injury to portions of said region that are adjacent to said internal structure,
    c) a signal measurement device for measuring said signal to determine occurrence of a maximum intensity of said signal during scanning of said region by said beam projector,
    d) a computing apparatus for associating said maximum intensity with a corresponding scanned location of said region, and
    e) a controlled source of therapeutic radiation for focussing a selected intensity of said therapeutic radiation at a target determined from said corresponding scanned location of said region.

9. A system as set forth in claim 8, wherein said investigative radiation comprises said therapeutic radiation.

10. A system as set forth in claim 9, wherein said sensor comprises a semiconductor diode capable of producing electric signals of an intensity that varies with the intensity of investigative radiation impinging upon said sensor during scanning of said region by said beam.

11. A system as set forth in claim 10, wherein said sensor comprises wires implanted in said living body, said wires connecting said semiconductor diode to said signal measurement device.

12. A system as set forth in claim 9, wherein said sensor comprises a scintillator material capable of producing light signals of an intensity that varies with the intensity of investigative radiation impinging upon said sensor during scanning of said region by said beam, and wherein said sensor comprises light-transmitting fibers connecting said scintillator material to said signal measurement device.

13. A method as set forth in claim 9, wherein said sensor comprises a piezoelectric material capable of producing acoustic signals of an intensity that varies with the intensity of investigative radiation impinging upon said sensor during scanning of said region by said beam, and wherein said signal measurement device comprises an acoustic microphone which is disposed external to said living body.

14. A method as set forth in claim 9, wherein said sensor comprises a piezoelectric material capable of producing electrical signals of an intensity that varies with the intensity of investigative radiation impinging upon said sensor during scanning of said region by said beam, and wherein said sensor comprises wires implanted in said living body, said wires connecting said piezoelectric material to said signal measurement device.

15. A system as set forth in claim 9, wherein said sensor comprises an x-ray emitting material capable of producing x-ray signals of an intensity that varies with the intensity of investigative radiation impinging upon said sensor during scanning of said region by said beam, and wherein said signal measurement device comprises an x-ray detector which is disposed external to said living body.

* * * * *